United States Patent [19]

de Ris et al.

[11] Patent Number: 4,637,735

[45] Date of Patent: Jan. 20, 1987

[54] BENCH-SCALE MATERIAL FLAMMABILITY TEST APPARATUS AND PROCESS FOR MEASURING FLAMMABILITY

[75] Inventors: John de Ris; George H. Markstein, both of Sharon, Mass.

[73] Assignee: Factory-Mutual Research Corporation, Norwood, Mass.

[21] Appl. No.: 823,124

[22] Filed: Jan. 27, 1986

Related U.S. Application Data

[63] Continuation of Ser. No. 569,651, Jan. 10, 1984, abandoned.

[51] Int. Cl.$^4$ ............................................. G01N 25/00
[52] U.S. Cl. ............................................. 374/8; 374/37; 422/80; 422/98; 436/148
[58] Field of Search ................. 73/36; 340/578; 374/8, 374/36, 37; 422/80, 98; 436/148

[56] References Cited

U.S. PATENT DOCUMENTS

| | | | |
|---|---|---|---|
| 3,148,531 | 9/1964 | Stoll et al. | 73/15 |
| 3,545,252 | 12/1970 | Springfield et al. | 73/15 |
| 3,593,563 | 7/1971 | Marmor et al. | 73/15.4 |
| 3,662,586 | 5/1972 | Suga | 73/15 R |
| 3,665,750 | 5/1972 | Dawn et al. | 73/15 R |
| 3,820,379 | 6/1974 | Nelson et al. | 73/15 R |
| 3,987,661 | 10/1976 | Kamp et al. | 73/15 R |
| 4,059,007 | 11/1977 | Miller et al. | 73/190 R |
| 4,076,873 | 2/1978 | Shea | 428/78 |

FOREIGN PATENT DOCUMENTS

1356023 6/1974 United Kingdom.

OTHER PUBLICATIONS

"Standard Test Method for Luminometer Numbers of Aviation Turbine Fuels", pp. 13–21, Designation D1740-75 (reapproved 1980).

"Standard Test Method for Smoke Point of Aviation Turbine Fuels", pp. 727–735, Designation D1322-75 (reapproved 1980).

"Development of a Heat Release Rate Calorimeter at NBS," by W. J. Parker and M. E. Long, *Ignition, Heat Release and Noncombustibility of Materials, ASTM STP* 502, American Society for Testing and Materials, 1982, pp. 135–151 (sponsored by the U.S. Navy).

"A Scientific Approach to Flame Radiation and Material Flammability" by John de Ris, presented at the Eighth U.S.–Japan Panel on Fire Research and Safety, Tsukuba, Japan, May 1985.

"Radiant Emission and Smoke-Points for Laminar Diffusion Flames of Fuel Mixtures," by George H. Markstein, abstract from presentation of Fall Technical Meeting of the Eastern Section, The Combustion Institute, Dec. 1984, Clearwater Beach, Fla.

"Rules for Estimating Sooting Tendencies of Complex Fuel Blends," by R. J. Gill, D. B. Olson and J. C. Pickens, AeroChem Research Laboratories, Inc., Princeton, N.J.

"Sooting Behavior of Gaseous Hydrocarbon Diffusion Flames and the Influence of Additives", K. P. Schug et al, Combustion Science and Technology, vol. 22, pp. 235–250, 1980.

"Effect of Molecular Structure on Incipient Soot Formation", H. F. Calcote et al, Combustion and Flame vol. 49, pp. 289–304, 1983.

*Primary Examiner*—Charles Frankfort
*Assistant Examiner*—W. Morris Worth
*Attorney, Agent, or Firm*—Lane & Aitken

[57] ABSTRACT

A bench-scale apparatus for measuring the heat-release rate of pyrolysis vapors of a material sample includes an oven having a heated chamber for receiving the sample, a flue and at least one entry port, a radiometer having a radiation sensor disposed in relation to the flue of the oven such that an area into which burning pyrolysis vapors are directed from the flue is adjacent to the radiation sensor, a fuel-gas control valve in communication with the entry port of the oven, and an electronic flow meter for measuring the amount of fuel-gas passing through the control valve, wherein signals from the radiometer operate the fuel-gas contral valve to provide an amount of fuel-gas sufficient to maintain a flame of the vapors at a predetermined height, and wherein the meter measures the amount of fuel-gas such that the measurement of the meter is used to indicate the heat-release rate of the pyrolysis vapors. An apparatus for measuring the sootiness of pyrolysis vapors of a material sample, including an oven, a smoke detector, a diluent control valve and an electronic flow meter is also disclosed, as well as processes for measuring large-scale flammability hazards of materials, sootiness of flames of materials, and heat-release rate of flames of materials.

19 Claims, 1 Drawing Figure

BENCH-SCALE MATERIAL FLAMMABILITY TEST APPARATUS AND PROCESS FOR MEASURING FLAMMABILITY

This application is a continuation of application Ser. No. 569,651, filed Jan. 10, 1984, abandoned.

BACKGROUND OF THE INVENTION

I. Field of the Invention

This invention pertains to a bench-scale flammability test apparatus and method for testing the flammability of a liquid or solid material.

II. Description of the Prior Art

There are a number of factors that determine the flammability of a material, many of which reflect the synergistic couplings between a burning fuel and its environment. These factors include (1) the imposed heat flux levels, (2) the geometric arrangement of the fuel, (3) the presence of other nearby materials and the nature of those fuels, and (4) the temperature, pressure and degree of vitiation of the surrounding atmosphere. In different situations, these factors can have a marked effect upon the flammability rankings of a material. In the prior art, flammability tests have attempted to take these factors into consideration, with varying degrees of success.

Unfortunately, many of the prior art material flammability tests available today attempt to infer large-scale flammability on the basis of bench-scale testing without properly taking into account an additional factor of great importance, that is, fire scale. It is now known that the relative flammability rankings of materials at small scale, such as that tested in a bench-scale apparatus, can be markedly different from the flammability rankings of those materials at large scale, due largely to the differences in burning mechanisms at small and large scales. One reason for the disparity between flammability characteristics at large and small scale is that, when a large amount of a fuel is pyrolized and burned, the flames are thicker and the radiative heat transfer from the flames can significantly increase the flammability hazards associated with the fuel. This radiation is generally unimportant at small scale, but dominant at large scale. Recent research has shown that the degree of radiation from various fuels at large scale is closely correlated with their sootiness, which is measured at small scale by the subject invention.

Heretofore, the test methods and apparatus of the prior art have attempted to remove the disparity between flammability measurements taken at bench scale and those taken at large scale by imposing an external radiant flux on the samples while measuring their heat release by combustion. Attempts are made thereby to infer large-scale flammability from these bench-scale tests. However, such methods and devices are inadequate for a number of important reasons. To begin with, they are typically cumbersome, require considerable chemical analysis equipment for measuring oxygen consumption, and allow the sample to be subjected to an undetermined added heat flux from the flames. Finally, prior art small-scale tests are unresponsive to the flames' own radiation and thus ignore an essential effect which controls the burning at large scale.

As a result, there is presently an inadequate correlation between the measurements derived from bench-scale flammability tests and actual flammability hazards on a large scale. Because bench-scale tests of the prior art fail to accurately indicate large-scale flammability, there is widespread mistrust of current standard flammability tests, and the art accordingly relies heavily on full-scale tests for flammability assessment. However, full-scale tests are very expensive, are difficult to reproduce, require such large samples that they cannot reasonably be considered for screening new materials under development and, since they are empirical, give little guidance for assessing hazards in related situations.

Thus, there is a need in the art for a bench-scale flammability test for measuring flammability properties of a sample of material, such that the measured properties are an accurate indication of the large-scale flammability properties of the material. The test should be compact and simple and free from the need for complicated equipment for chemical analysis. The present invention meets these objectives and other objectives which will become apparent from the following detailed description.

SUMMARY OF THE INVENTION

In accordance with the present invention, a bench-scale apparatus for measuring the heat-release rate and sootiness of pyrolysis vapors of a material sample includes an oven that is provided with a flue and a heated chamber for containing a sample, a radiometer having a radiation sensor located above the flue so that it can sense the tip of the flame from the burning pyrolysis gases, and an optical smoke detector located above the radiometer so that it can sense any visible smoke emerging from the flame tip. These two sensors provide a means for simultaneously indicating the heat-release rate and sootiness of the pyrolysis vapors. Additional fuel-gas is supplied to the oven through an entry port to augment the flame height and heat-release rate. This fuel-gas supply has a fuel-gas control valve in communication with the port and an electronic flow meter for measuring the amount of added fuel-gas passing through the fuel-gas control valve. Signals from the radiometer operate the fuel-gas control valve to provide an amount of fuel-gas just sufficient to maintain a flame tip at a predetermined height, so that the measurements of the meter are used to indicate the relative heat-release rate of the pyrolysis vapors. The means for indicating sootiness includes a diluent control valve also in communication with the entry port and a second electronic flow meter for measuring the amount of diluent passing through the diluent control valve. Signals from the smoke detector operate the diluent control valve to provide an amount of diluent sufficient to maintain the sootiness of the flame at a predetermined point, so that the measurements of the second meter are used to indicate the sootiness of the pyrolysis vapors. A process for indicating large-scale flammability hazard of a material is also described, and includes the steps of heating a small-scale sample of the fuel, measuring the sootiness of pyrolysis vapors of the heated sample, and indicating the large-scale flammability hazard, whereby a higher sootiness of the flame indicates a higher large-scale flammability hazard and a lower sootiness of the flame indicates lower large-scale flammability hazard.

DESCRIPTION OF THE PREFERRED EMBODIMENTS

Figure 1:
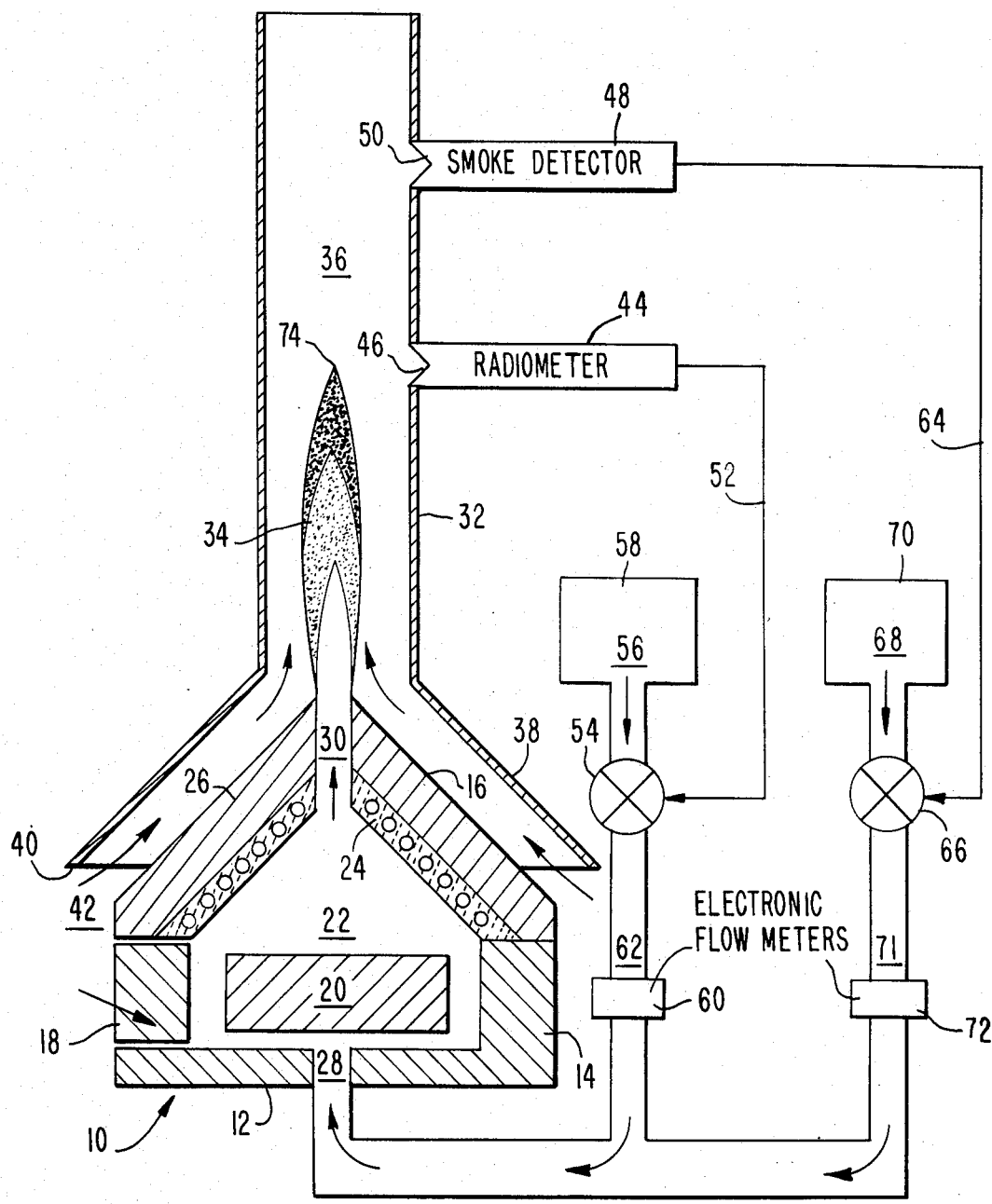
FIG. 1 depicts an apparatus in accordance with a preferred embodiment of the present invention.

It has now been discovered that the disparity between small-scale flammability tests of materials and large-scale flammability hazards that is due to the radiant emission of a large-scale flame can be quantified by measuring the sootiness of the flame of a sample of the material. Fuels which generate copious amounts of soot tend to have highly radiative flames, and this results in higher large-scale burning rates. By taking the degree of flame sootiness into consideration, the present invention provides a bench-scale flammability test that much more accurately predicts large-scale flammability hazards.

In order to measure flame sootiness and thus quantify the effect of radiant emission for a particular sample, the present invention provides a test apparatus that determines the sootiness by measuring the amount of diluent necessary to maintain a bench-scale flame at a predetermined soot point. The invention also provides an apparatus that determines the heat-release rate in an improved fashion by measuring the amount of fuel-gas necessary to maintain the small bench-scale flame at a predetermined height.

The present invention will now be described in greater detail in connection with the embodiment depicted in FIG. 1. In this embodiment, an oven 10 is provided with a bottom 12, wall 14 and top 16. A door 18 is disposed in a portion of wall 14 so that a sample 20 can be inserted into sample chamber 22. The oven 10 can be composed of any suitable materials that are not adversely affected by the heating of the sample. The ceiling 24 of the sample chamber can be composed of a suitable refractory material and covered with insulation 26.

Sample 20 is of a relatively small size. In the embodiment depicted in FIG. 1, the sample has the dimensions $2'' \times 2'' \times 1''$ deep. The present invention is especially adapted for testing the flammability of solid samples, such as sample 20, but inventive features of the present invention can be applied to the testing of the flammability of liquid samples after modifications are made that are within the skill of the art.

Bottom 12 of the oven defines an entry port 28 and the top 16 defines a flue 30. As depicted by the arrows in the drawing, gases circulate upwardly through chamber 22. Thus, fuel-gas and diluent gas enter through port 28 and pyrolysis vapors derived from the heating of sample 20 exit through flue 30.

After exiting through the flue, the pyrolysis vapors enter into chimney 32 that is disposed above flue 30. Thus, an area 36 encompased by chimney 32 receives the pyrolysis vapors directed from the flue and, as depicted in FIG. 1, these vapors include a flame 34. The pyrolysis vapors can also include smoke that would be disposed above flame 34 in the area 36 encompassed by the chimney.

Chimney 32 is widened and receives top 16 of the oven at a widened portion 38. At the lower periphery 40 of this widened portion, an annular opening 42 is provided for the entry of an oxygen-containing gas, such as air, to supply the flame 34. As indicated by the arrows in FIG. 1, air entering openings 42 passes upwardly through widened portion 38 and comes into contact with the heated gases contained in area 36 of the chimney. Thus, in the depicted preferred embodiment, burning occurs in area 34 and not in chamber 22.

A radiometer 44 having a radiation sensor 46 is disposed above flue 30 so that the radiation sensor is adjacent to area 36 into which the pyrolysis vapors are directed from the flue. Similarly, smoke detector 48, having smoke sensor 50, is disposed in relation to the flue so that the smoke sensor is adjacent to area 36 as well. As depicted in the figure, the radiometer is disposed below the smoke detector. In the embodiment depicted in FIG. 1, chimney 32 is a glass chimney provided with holes so that radiation sensor 46 and smoke sensor 50 can sense the presence of radiation and smoke, respectively, without being obscured by the chimney.

Flame 34 is maintained at a constant height by virtue of a flame height control loop that comprises radiometer 44, whereby the flame tip 74 is maintained in proximity to sensor 46. The radiation sensor 46 senses the flame delivers signals through cable 52 to a fuel-gas control valve 54. Through this arrangement, fuel-gas 56 is delivered from fuel-gas supply 58 in an amount sufficient to maintain flame 34 at a predetermined height. When radiation sensor 46 senses that the flame height is too low, it sends a signal to valve 54 to release excess fuel-gas that, in turn, causes increased combustion and a heightened flame. In the embodiment depicted in FIG. 1, fuel-gas 56 is ethane, but any suitable fuel-gas is satisfactory in the practice of the invention.

Electronic flow meter 60 is disposed in the path 62 of the fuel-gas line, such that fuel-gas released by valve 54 is measured by the meter. These measurements are recorded over an extended period of time and are used to determine the relative heat-release rate of the sample in accordance with the observation that larger amounts of fuel-gas indicate a lesser sample heat-release rate and smaller amounts of fuel-gas indicate a greater sample heat-release rate.

A soot-point control loop is also provided, beginning with smoke detector 48. The purpose of the soot-point control loop is to maintain the sootiness of the pyrolysis vapors in area 36 at a predetermined value. Preferably, this predetermined value is related to the soot-point of the flame, i.e., the maximum height that the flame can attain without releasing soot. Since, in this embodiment, the flame height is kept constant, the soot-point is that point at which the least amount of inert gas can be added without causing the flame to release soot.

Thus, smoke sensor 50 senses smoke, i.e., soot, and sends signals through cable 64 to operate diluent control valve 66. Diluent 68, contained in supply 70, is in this fashion introduced into diluent path 71 and, eventually, through port 28 and into heated chamber 22. Diluent 68 can be any suitable inert gas and, in the embodiment depicted in FIG. 1, the diluent is nitrogen. Flame 34 is thus continuously maintained in its marginal soot-point state by smoke detector 48 which increases the supply of inert gas when the pyrolysis vapors increase in sootiness. The increase in inert gas flow suppresses the soot formation without changing the flame height.

A second electronic flow meter 72 is disposed in the path 71 of diluent 68, so that the amount of diluent flowing through path 71 is measured on a continuous basis. These measurements provide an instantaneous indication of pyrolysis vapor sootiness and, by inference, the radiant emission of a large-scale amount of the material that is being tested.

Thus, the embodiment in FIG. 1 provides a compact, simple way to determine precisely the heat-release rate and sootiness of pyrolysis vapors of a sample. In another embodiment, the flame height control loop is eliminated, whereby only the sample sootiness is measured. In still another embodiment, the soot-point control loop is eliminated, whereby only the sample heat-release rate is measured.

Throughout this application, the term "bench-scale" is used to describe the size of the test apparatus and process of this invention. As used herein, the term is meant to define a scale that is designed for a material sample portion that is relatively small compared to a portion size that is normally encountered in the actual use of the material. Thus, the actual size of the bench-scale sample and related apparatus for measuring flammability can vary considerably, as long as the sample is of such a small size that the phenomenon of fire scale might become a factor.

Having thus described the present invention in terms of numerous specific embodiments, it will be readily apparent to those skilled in the art that numerous modifications and additions can be made without departing from the spirit and scope of the invention.

We claim:

1. A bench-scale apparatus for measuring the heat-release rate of pyrolysis vapors of a material sample comprising
   an oven defining a heat chamber for receiving said sample, a flue, and at least one entry port,
   a radiometer having a radiation sensor disposed in relation to said flue such that an area into which burning pyrolysis vapors are directed from said flue is adjacent to said radiation sensor,
   a flue-gas control valve in communication with said port, and
   an electronic flow meter for measuring the amount of fuel-gas passing through said control valve,
   wherein signals from said radiometer operate said fuel-gas control valve to provide an amount of fuel-gas sufficient to maintain a flame of said vapors at a predetermined height, and wherein said meter measures said amount of fuel-gas such that the measurement of said meter is used as an indication of the heat-release rate of said pyrolysis vapors, whereby larger amounts of measured fuel-gas indicate lesser sample heat release rates and smaller amounts of fuel-gas indicate greater sample heat release rates.

2. The apparatus of claim 1, further comprising
   a smoke detector having a smoke sensor disposed in relation to said flue such that said area is adjacent to said smoke sensor,
   a diluent control valve in communication with said port, and
   a second electronic flow meter for measuring the amount of diluent passing through said diluent control valve,
   wherein signals from said smoke detector operate said diluent control valve to provide an amount of diluent sufficient to maintain the sootiness of said flame at a predetermined level, and wherein said second meter measures said amount of diluent such that the measurement of said second meter is used as in indication of the sootiness of said pyrolysis vapors, whereby larger amounts of measured diluent indicate greater sootiness and smaller amounts of measured diluent indicate lesser sootiness.

3. The apparatus of claim 1, wherein said predetermined height is the height at which the tip of said flame is proximate to said radiometer.

4. The apparatus of claim 2, wherein said predetermined level is the soot-point of said flame.

5. The apparatus of claim 1, further comprising a chimney, wherein said area is disposed within said chimney and said sensor is disposed on a wall of said chimney and is in communication with said area.

6. The apparatus of claim 5, wherein said chimney has at least one opening for introducing an oxygen-containing gas adjacent to said flue.

7. A bench-scale apparatus for measuring the sootiness of burning pyrolysis vapors of a material sample that produce smoke comprising
   an oven defining a heat chamber for receiving said sample, a flue, and at least one entry port,
   a smoke detector having a smoke sensor disposed in relation to said flue such that an area into which burning pyrolysis vapors are directed from said flue is adjacent to said smoke sensor,
   a diluent control valve in communication with said port,
   and an electronic flow meter for measuring the amount of diluent passing through said diluent control valve,
   wherein signals generated by said smoke detector in response to smoke produced by said vapors operate said diluent control valve to provide an amount of diluent sufficient to maintain the sootiness of a flame at a predetermined level, and wherein said meter measures said amount of diluent such that the measurement of said meter is used as an indication of the sootiness of said pyrolysis vapors, whereby larger amounts of measured diluent indicate greater sootiness and smaller amounts of measured diluent indicate lesser sootiness.

8. The apparatus of claim 7, wherein said predetermined level is the soot-point of said flame.

9. The apparatus of claim 7, further comprising a chimney, wherein said area is disposed within said chimney and said sensor is disposed on a wall of said chimney and is in communication with said area.

10. The apparatus of claim 9, wherein said chimney has at least one opening for introducing an oxygen-containing gas into said chimney adjacent to said flue.

11. A bench-scale process for determining sootiness of a flame of a material sample, comprisng the steps of heating a sample of said material in a chamber to produce pyrolysis vapors, igniting said vapors to produce a flame, maintaining the sootiness of said flame at a predetermined level by supplying a variable amount of a diluent to said chamber, measuring the variable amount of diluent supplied, and using said measurement as an indication of sootiness of said fuel, whereby larger amounts of diluent indicate greater sootiness and smaller amounts of diluent indicate lesser sootiness.

12. The process of claim 11 wherein said predetermined level is the soot-point of said flame.

13. The process of claim 11, wherein said indication of sootiness is used to indicate large-scale flammability hazard, whereby a higher sootiness of the flame of said sample indicates a higher large-scale flammability hazard and a lower sootiness of the flame of said sample indicates lower large-scale flammability hazard.

14. The process of claim 11, wherein said process further determines heat-release rate of said flame and further comprises the steps of maintaining said flame at a predetermined height by supplying a variable amount of fuel-gas to said chamber, measuring the variable amount of fuel-gas supplied, and using said measurement as an indication of the heat-release rate of said fuel from said measurement, whereby larger amounts of fuel-gas indicate a lesser heat-release rate and smaller amounts of fuel-gas indicate a greater heat-release rate.

15. The process of claim 14, wherein said sootiness and heat-release rate are used to indicate large-scale flammability hazard, whereby a higher sootiness of the flame of said sample indicates higher large-scale flammability hazard and a lower sootiness of the flame of said sample indicates lower large-scale flammability hazard, and whereby a higher heat-release rate indicates higher large-scale flammability hazard and a lower heat-release rate indicates lower large-scale flammability hazard.

16. The process of claim 11, wherein said material is a solid material.

17. A bench-scale process for determining the heat-release rate of a flame of a material, comprising the steps of heating a sample of said material in a chamber to produce pyrolysis vapors, igniting said vapors to produce a flame, maintaining said flame at a predetermined height by supplying a variable amount of fuel-gas to said chamber, measuring the variable amount of fuel-gas supplied, and using said measurement as an indication of the heat-release rate of said fuel from said measurement, whereby larger amounts of fuel-gas indicate a lesser heat-release rate and smaller amounts of fuel-gas indicate a greater heat-release rate.

18. The process of claim 17, wherein said heat-release rate is used to indicate large-scale flammability hazard, whereby a higher heat-release rate indicates higher large-scale flammability hazard and a lower heat-release rate indicates lower large-scale flammability hazard.

19. A process for measuring large-scale flammability for a material having a conventional flammability ranking at a small-scale that is different from the material's conventional flammability ranking at large-scale due to the phenomenen of fire scale, said process comprising the steps of
providing a bench-scale sample of said material,
introducing said sample into a bench-scale apparatus provided with a means for determining sootiness of pyrolysis vapors,
determining a sootiness of burning pyrolysis vapors of said sample, and
using said sootiness to determine a large-scale flammability for said material, said large-scale flammability being unaffected by the effect of fire scale, whereby a higher sootiness of the burning pyrolysis vapors of the sample indicates higher large-scale flammability and a lower sootiness of the burning pyrolysis vapors of the sample indicates lower large-scale flammability.

* * * * *